United States Patent
Perricone

(10) Patent No.: US 6,417,226 B1
(45) Date of Patent: Jul. 9, 2002

(54) SKIN WHITENERS CONTAINING HYDROXYTETRONIC ACID

(76) Inventor: Nicholas V. Perricone, 27 Coginchaug Ct., Guilford, CT (US) 06437

( * ) Notice: Subject to any disclaimer, the term of this patent is extended or adjusted under 35 U.S.C. 154(b) by 0 days.

(21) Appl. No.: 09/735,144

(22) Filed: Dec. 12, 2000

(51) Int. Cl.$^7$ .................. A61K 31/34; A61K 7/021
(52) U.S. Cl. ................................ 514/474; 424/63
(58) Field of Search .................. 514/474; 424/63

(56) References Cited

U.S. PATENT DOCUMENTS

| | | | |
|---|---|---|---|
| 3,620,744 A | * | 11/1971 | Schellenberg |
| 5,091,171 A | * | 2/1992 | Yu et al. |
| 5,262,153 A | | 11/1993 | Mishima et al. |
| 5,385,938 A | * | 1/1995 | Yu et al. |
| 5,602,259 A | * | 2/1997 | Boo et al. |
| 5,643,961 A | * | 7/1997 | Yu et al. |
| 5,654,336 A | * | 8/1997 | Yu et al. |
| 5,747,006 A | | 5/1998 | Dornoff et al. |
| 5,932,612 A | | 8/1999 | Gordon et al. |
| 5,980,904 A | | 11/1999 | Leverett et al. |
| 6,010,685 A | | 1/2000 | Ziemniak et al. |
| 6,057,360 A | | 5/2000 | Gordon et al. |
| 6,068,834 A | | 5/2000 | Kvalnes et al. |
| 6,077,503 A | | 6/2000 | Dornoff |
| 6,139,854 A | | 10/2000 | Kawato |
| 6,265,436 B1 | * | 7/2001 | Appere et al. |

OTHER PUBLICATIONS

Willis, I., Skin & Aging Supp., Nov. 2000, 17–21.
Morganti et al., An innovative cesmeceutical . . . , Database CAPLUS, AN2000:373138, abstract, J. Appl. Cosmetol., 1999, vol. 17(4), pp. 144–153.*
Weyde, Bleaching of photographs . . . Database Caplus, AN1958:102874, abstract of Patent, DE946327, 1956.*
Okada et al, Photographic processing using a novel . . . , Database USPATFUL, AN 96:75265, abstract of Patent U.S. 5547817, 1996.*
Roomi et al., Growth suppression of malignant leukenia cell line . . . , Database Caplus, AN 1997:747923, abstract, Cancer Lett. 1998, vol. 122/1,2, pp. 93–99.*

* cited by examiner

Primary Examiner—William R. A. Jarvis
Assistant Examiner—Vickie Kim
(74) Attorney, Agent, or Firm—Mary M. Krinsky

(57) ABSTRACT

Skin whitening compositions contain α-hydroxytetronic acid or a α-hydroxy tetronic derivative, and, in some cases, hydroquinone, an α-hydroxy acid such as glycolic acid, and a fatty acid ester of ascorbic acid such as ascorbyl palmitate.

11 Claims, No Drawings

SKIN WHITENERS CONTAINING HYDROXYTETRONIC ACID

STATEMENT REGARDING FEDERALLY SPONSORED RESEARCH

Not Applicable

BACKGROUND OF THE INVENTION

1. Field of the Invention

This invention relates to the use of hydroxytetronic acid and/or hydroxytetronic acid derivatives alone, or in combination with other ingredients such as hydroquinone, glycolic acid, and/or ascorbyl palmitate, in compositions that whiten skin, and methods for using the compositions.

2. Description of Related Art

A variety of dermatological compositions have been suggested for skin whitening to improve the appearance of hyperpigmentary skin conditions such as that observed as freckles, melasma, café au lait and liver spots spots, and lesions observed in Addison's disease, hemochromatosis, vitiligo, piebaldism, phenylketonuria, and the like, and/or for cosmetic purposes. Skin color is primarily determined by the amount of melanin present in epidermal cells, so many modern skin bleaching compositions either destroy melanin (typically by destroying or disrupting melanin granules) or inhibit its formation (often by inhibiting tyrosinase, a melanin biosynthetic enzyme, or melanocyte activity), or both. Many of these contain harsh chemicals such as peroxides, acids or formaldehyde, or thiolated materials such as glutathione, cysteine, mercaptosuccinic acid, mercaptodextran, and mercaptoethanol, which have an objectionable odor that makes products containing them undesirable to a consumer (discussed in U.S. Pat. No. 5,980,904 to Leverett and Dornoff, U.S. Pat. No. 5,747,006 to Dornoff, et al., and U.S. Pat. No. 6,077,503 to Dornoff; these and subsequent references are hereby incorporated herein in their entireties by reference).

Less stringent therapies have other disadvantages. The only treatment for hyperpigmentation that is approved in the United States for use by consumers without a prescription, for example, is the topical application of hydroquinone, which acts by suppressing melanocyte activity. Hydroquinone is oxidized by air, light, and tyrosinase itself, however, which adversely effects the shelf life of preparations containing it and its bioavailability upon application. Hydroquinone can cause burning, redness, sensitization and irritation in some persons, particularly after application of quantities sufficient to cause skin bleaching as it requires prolonged treatment before results are noticeable, and its oxidized products have been implicated in skin irritation and pigmentation rebound (U.S. Pat. No. 6,068,834 to Kvalnes, et al.). Topical retinoids and topical corticosteroids have been suggested as hypopigmenting agents, as have laser treatment and chemical peels, but these fall short of desirable responses. A new combination therapy recently suggested combines tretinoin and fluocinolone with hydroquinone (Willis, I., *Skin & Aging Supp.*, Nov. 17–21, 2000). Kojic acid and arbutin have also been suggested, but these are marginal tyrosinase inhibitors and are not very bioavailable and thus have disappointing efficacy.

Other pleasanter compositions recently suggested employ natural materials, which have in some cases been used for centuries in Asia or Europe to bleach skin and skin areas, or enhance the appearance of fair skin. These include the use of lemon, orange, cucumber, ginko, carob, rose fruit, geraniuim herb, cinnamon, sweet marjoram, rosemary, clove, mulberry, licorice, bearberry, and acerola cherry extracts (ibid.). The variability of active ingredients in these natural products sometimes limits their usefulness, particularly as skin type, color, age, and condition of vary greatly in different subjects, and make suggested dosages and regimens difficult to fashion. And other ingredients in the mixtures can cause allergic reactions in sensitive persons.

It would be desirable to have alternative preparations, and/or ones that improve the efficacy of presently known skin whitening agents.

BRIEF SUMMARY OF THE INVENTION

It is an objective of the invention to provide new compositions for whitening skin and methods for their use. It is a further objective to provide compositions that can be used to enhance known skin whitening compositions and treatments.

These objectives are achieved by the present invention, which provides methods and compositions for whitening skin through the topical application of α-hydroxytetronic acid and/or a-hydroxytetronic derivatives, in a preparation that typically includes a dermatologically acceptable carrier. In many embodiments, the α-hydroxytetronic active ingredient is applied to skin in combination with at least one adjunct ingredient such as hydroquinone, an α-hydroxy acid such as glycolic acid, and a fatty acid ester of ascorbic acid such as ascorbyl palmitate. Some preferred embodiments contain from about 0.5% to about 25% by weight α-hydroxytetronic acid and/or hydroxytetronic acid derivatives alone, or in combination with hydroquinone, glycolic acid and/or ascorbyl palmitate.

BRIEF DESCRIPTION OF THE INVENTION

This invention is based upon the finding that α-hydroxytetronic acid, alone or in combination with hydroquinone, provides significant bleaching when applied to the skin, without undesirable side effects.

In the practice of the invention, a composition containing an effective amount of α-hydroxytetronic acid active ingredient, i.e., α-hydroxytetronic acid, a derivative, or mixtures thereof, is applied to skin to whiten it. By "whitening" is meant the visually apparent reduction in skin pigmentation observed qualitatively and sometimes measured using an assay such as Melanoderm in vitro assays that quantify changes in melanin formation in cultured mammalian epidermal cells. Alpha-hy-droxytetronic acid (sometimes called 2-hydroxytetronic acid) may be thought of as ascorbic acid without a side chain; the enol form, 3,4-dihydroxy-2-(5H) furnanone, has the formula

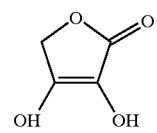

Alpha-hydroxytetronic acid derivatives include, but are not limited to, acylated α-hydroxytetronic acid derivatives, particularly $C_1$ to $C_6$ (hereinafter referred to as "lower") straight- or branched-chain alkyl esters; hyroxytetronic acid salts, particularly sodium, potassium, and magnesium salts (hereinafter collectively referred to as "physiologically acceptable salts"); alkyl derivatives, particularly lower, or $C_1$ to $C_8$, alkyls, i.e., derivatives having a methyl-, ethyl-, and propyl- group in the γ- (4-) position (sometimes called, respectively, tetrinic, pentinic, and hexinic acid), and their esters and salts, particularly lower alkyl esters and their physiologically acceptable salts); cycloaliphatic derivatives, i.e., derivatives having alkyl hydrocarbon side chains which are closed to form a ring structure, particularly those having a hydrocarbon ring structure containing from 3 to 6 carbon atoms attached to the γ- (4-) position; alkoxy derivatives, particularly those having a lower alkyl group attached to the molecule in the α- (2-), β- (3-), or γ- (4-) position by oxygen such as methoxy-, ethoxy-, propoxy-, and isopropoxy- derivatives, and the like; aryl derivatives, particularly those having a phenyl, benzyl, tolyl, or phenethyl group in the γ- (4-) position, and substituted aryls, notably halogenated derivatives such as those having a chlorophenyl or dichlorophenyl group attached to the γ- (4-) position; their lower alkyl esters and physiologically acceptable salts; and mixtures thereof. For convenience, as used herein, the term "hydroxytetronic acid" includes α-hydroxytetronic acid itself, alone or in combination with known derivatives, esters, salts, and the like. Specifically encompassed are optical isomers and racemic mixtures, and natural vitamin C mixtures enriched with α-hydroxytetronic acid and/or its derivatives.

Typical compositions of the invention contain from about 0.5% to about 25% by weight, more narrowly from about 2% to about 15% by weight, and even more narrowly from about 3% to about 10% by weight, α-hydroxytetronic acid and/or a derivative thereof. Lower concentrations may be employed for less pronounced hyperpigmentation conditions and in sunscreens and sunblocks used after skin whitening treatment (more fully discussed below), and higher concentrations may be employed with more acute pigmentation conditions. Suggested ranges also depend upon any adjunct ingredients employed in the compositions (more fully discussed below) and the user's coloring and skin type as well as the extent of severity of the hyperpigmentation problem. Some embodiments contain from about 1% to 10%, more narrowly from about 2% to about 5 %, even more narrowly from about 3 % to about 4% by weight hydroxytetronic acid; others contain from about 7% to about 25%, more narrowly from about 10% to about 15%, by weight hydroxytetronic acid. As a practical matter, however, to avoid the need for repeated application, it is desirable that the topically applied composition be formulated to contain at least about 3to 5% by weight hydroxytetronic acid, and many embodiments contain about 10% or higher.

As summarized above, some whitening compositions of the invention contain at least one other adjunct ingredient in addition to hydroxytetronic acid. Adjunct ingredients include, but are not limited to, hydroquinone, α-hydroxy acids, and fatty acid esters of ascorbic acid. Many embodiments employ more than one adjunct ingredient. Especially preferred bleaching compositions contain hydroquinone (sometimes also called p-dihydroxybenzene or 1,4 benzenediol) in addition to the hydroxytetronic active ingredient. Typical hydroquinone concentrations range from about 0.25% to about 25% by weight, more narrowly from about 1% to about 5%, and even more narrowly from about 2% to about 4% by weight.

As used herein, the term "α-hydroxy acid" has reference to and encompasses the general class of organic compounds containing at least one hydroxy group and at least one carboxyl group, and wherein at least one hydroxyl group is located on the α-carbon atom. Typically, the compounds are organic acids having at least one carboxylic acid group and at least one hydroxyl group on the α-carbon atom, and may contain other functional groups including additional hydroxyl and carboxylic acid moieties. Preferred α-hydroxy acids and/or α-hydroxy acid derivatives are those which are less bulky structurally, typically having a one- to three-carbon backbone, so that they penetrate the skin well such as those set out in U.S. Pat. No. 5,965,618 at column 6 lines 4 to 29. Where employed, glycolic and/or lactic acid or their derivatives are preferred; glycolic acid is especially efficacious. Lactic acid was suggested as a skin-whitening agent in U.S. Pat. No. 5,262,153 to Mashima, et al. Typical hydroxy acid concentrations range from about 1% to about 25% by weight, more narrowly from about 2% to about 15%, and even more narrowly from about 3% to 10% by weight. As with the hydroxytetronic acid ingredient, higher concentrations may be employed for more acute conditions. In some embodiments, for example, from about 8% to 12% may be employed; in others, ranges of from about 3% to about 7% by weight are sufficient. One efficacious composition of the invention contains about 10% hydroxytetronic acid, about 10% glycolic acid, and about 4% hydroquinone.

Fat-soluble fatty acid esters of ascorbic acid (vitamin C) are employed as alternate or additional adjunct ingredients in other embodiments, alone or in combination with hydroquinone or α-hydroxy acids. The more oxidation-resistant saturated fatty acid esters of ascorbic acid are preferred, including, but not limited to, ascorbyl laurate, ascorbyl myristate, ascorbyl palmitate, ascorbyl stearate, and ascorbyl behenate. Ascorbyl palmitate is used in one embodiment. As denoted herein, where fatty acid esters are described, e.g., ascorbyl stearate, compositions having predominantly that ester, e.g., predominantly stearate, are included. The esters may be prepared using hydrogenated oils or fats, or fractions thereof, and contain small amounts of another ester. Ascorbyl stearate prepared using canola, for example, commonly contain about 4% ascorbyl palmitate. It is an advantage of the invention that where fatty acid esters of ascorbic acid are employed as an adjunct ingredient, they help provide emollient properties to the composition. Typical concentration ranges of ascorbyl palmitate vary from about 0.25% to about 10%, more narrowly from about 2% to about 8%, and even more narrowly from about 3% to about 5% by weight.

However, only effective amounts of active ingredient(s) are needed to whiten skin, so generally topical application to skin sites is accomplished in association with a carrier, and particularly one in which the active ingredient is soluble per se or is effectively solubilized (e.g., as an emulsion or microemulsion). Where employed, the carrier is inert in the sense of not bringing about a deactivation or oxidation of active or adjunct ingredient(s), and in the sense of not bringing about any adverse effect on the skin areas to which it is applied. In one preferred practice of the invention, hydroxytetronic acids are applied in admixture with a dermatologically acceptable carrier or vehicle (e.g., as a lotion, cream, ointment, soap, stick, or the like) so as to facilitate topical application and, in some cases, provide additional beneficial effects as might be brought about, e.g., by moisturizing of the affected skin or mucosal areas. While the carrier for dermatological compositions can consist of a relatively simple solvent or dispersant such as water, it is generally preferred that the carrier comprise a composition more conducive to topical application, and particularly one which will form a film or layer on the skin to which it is applied so as to localize the application and provide some resistance to washing off by immersion in water or by perspiration and/or aid in the percutaneous delivery of the active agent. Many preparations are known in the art, and include lotions containing oils and/or alcohols and emollients such as olive oil, hydrocarbon oils and waxes, silicone oils, other vegetable, animal or marine fats or oils, glyceride derivatives, fatty acids or fatty acid esters or alcohols or alcohol ethers, lecithin, lanolin and derivatives, polyhydric alcohols or esters, wax esters, sterols, phospholipids and the like, and generally also emulsifiers (nonionic, cationic or anionic), although some of the emollients inherently possess emulsifying properties. These same general ingredients can be formulated into a cream rather than a lotion, or into gels, or into solid sticks by utilization of different proportions of the ingredients and/or by inclusion of thickening agents such a s gums or other forms of hydrophilic colloids. One preferred embodiment is an oil-in-water cream. Such compositions a re referred to herein as dermally, dermatologically, or pharmaceutically acceptable carriers.

Suitable carriers include water, alcohols, oils and the like, chosen for their ability to dissolve or disperse ingredients used in the treatment. In some embodiments, active and/or adjunct ingredients are added to a sunscreen or sunblock formulations so that topical application has the further advantage of preventing repigmentation during and/or after treatment. Preferred formulae of this type are SPF 15 or higher. Many of these preferred embodiments contain titanium dioxide or zinc oxide which additionally soothe and lubricate the skin and help minimize side effects in sensitive skin and with formulations containing high concentrations of bleaching ingredients.

Generally in the practice of methods of the invention, the composition is topically applied to darkened skin areas in a predetermined or as-needed regimen either at intervals by application of a lotion or the like, it generally being the case that gradual lightening is noted with each successive application. Insofar as has been determined based upon clinical studies to date, no adverse side effects are encountered. It is an advantage of the invention that it can be used to augment other skin lightening treatments including, but not limited to, those discussed above such as topical administration of hydroquinone, hydroquinone and glycolic acid, and kojic acid.

The above description is for the purpose of teaching the person of ordinary skill in the art how to practice the present invention, and it is not intended to detail all those obvious modifications and variations of it which will become apparent to the skilled worker upon reading the description. It is intended, however, that all such obvious modifications and variations be included within the scope of the present invention, which is defined by the following claims. The claims are intended to cover the claimed components and steps in any sequence which is effective to meet the objectives there intended, unless the context specifically indicates the contrary.

What is claimed is:

1. A method for whitening skin comprising topically administering to the skin an effective amount of a composition containing from about 0.5% to about 25% by weight of unsubstituted $\alpha$-hydroxytetronic acid.

2. A method according to claim 1 wherein the composition contains from about 2% to about 15% by weight active ingredient.

3. A method according to claim 1 wherein the composition contains from about 3% to about 10% active ingredient.

4. A method according to claim 1 wherein the composition further comprises at least one adjunct ingredient selected from the group consisting of hydroquinone, an $\alpha$-hydroxy acid, a fatty acid ester of ascorbic acid, and mixtures thereof.

5. A method according to claim 4 wherein one adjunct ingredient is hydroquinone.

6. A method according to claim 4 wherein one adjunct ingredient is glycolic acid.

7. A method according to claim 4 wherein one adjunct ingredient is ascorbyl palmitate.

8. A method for whitening skin comprising applying to the skin a composition containing from about 0.5% to about 25% by weight of unsubstituted $\alpha$-hydroxytetronic acid and at least one adjunct ingredient selected from the group consisting of hydroquinone, an $\alpha$-hydroxy acid, and a fatty acid ester of ascorbic acid.

9. A method according to claim 8 wherein an adjunct ingredient is hydroquinone.

10. A method according to claim 8 wherein an adjunct ingredient is glycolic acid, ascorbyl palmitate, or mixtures thereof.

11. A method according to claim 8 wherein the composition contains from about 0.5% to about 25% by weight $\alpha$-hydroxytetronic acid and from about 0.25% to about 25% by weight adjunct ingredient.

* * * * *